(12) United States Patent
Brinkmann et al.

(10) Patent No.: US 6,270,988 B1
(45) Date of Patent: Aug. 7, 2001

(54) PROCESS FOR PRODUCING RECOMBINANT PROTEINS USING A GENE FOR TRNA

(75) Inventors: Ulrich Brinkmann, Hamm; Ralf Mattes, Stuttgart; Stephan Fischer, Weilheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/009,423

(22) Filed: Jan. 27, 1993

Related U.S. Application Data

(63) Continuation of application No. 07/435,623, filed on Nov. 13, 1989, now abandoned.

(30) Foreign Application Priority Data

Nov. 11, 1988 (DE) .................................. 38 38 378
Aug. 31, 1989 (DE) .................................. 39 28 899
Sep. 25, 1989 (DE) .................................. 39 31 933

(51) Int. Cl.[7] .............................. C12P 21/02; C12N 5/02; C12N 15/70
(52) U.S. Cl. .................... 435/69.1; 435/71.2; 435/320.1; 435/375
(58) Field of Search .................. 435/69.1, 71.2, 435/375, 320.1

(56) References Cited

U.S. PATENT DOCUMENTS 4,673,641 * 6/1987 George et al. .................. 435/69.1
4,970,147 * 11/1990 Huala et al. .................. 435/69.1
5,145,776 * 9/1992 Tabor et al. .................. 435/91.5

FOREIGN PATENT DOCUMENTS 0141790 10/1984 (EP) .
2135677 2/1984 (GB) .

OTHER PUBLICATIONS

Georgiou, Aiche Journal, vol. 34, No. 8, pp. 1233–1248 (1988).*
Ulrich, et al., Biol. Abst. 83: 79171 (1987).
Mullin et al. (1984), Cell, vol. 37, pp. 669–674.*
Neill et al. (1987), Gene, vol. 55, pp. 303–317.*
Masson et al. (1987), Journal of Cell. Biochem., vol. 11C, p. 195.*
Robinson et al. (1984), Nucleic Acid Res., vol. 12, pp. 6663–6671.*
Bonekamp et al. (1988), Nucleic Acid Res., vol. 16, pp. 3013–3024.*
Ulrich et al. (1986), Mol. Gen. Genet., vol. 205, pp. 540–545.*

* cited by examiner

Primary Examiner—Terry McKelvey
(74) Attorney, Agent, or Firm—Fulbright & Jaworski, LLP

(57) ABSTRACT

The present invention provides a process for the expression of a recombinant gene, which contains AGA and/or AGG codons for arginine, in *Escherichia coli* after transformation with an expression vector which contains the recombinant gene, wherein the amount of t-RNA present in the *E. coli* cells which incorporates arginine and recognises the codons AGG and AGA is increased to at least fivefold of the amount normally occurring in these cells.

10 Claims, 1 Drawing Sheet

PROCESS FOR PRODUCING RECOMBINANT PROTEINS USING A GENE FOR TRNA

This application is a continuation of application Ser. No. 07/435,623, filed Nov. 13, 1989, now abandoned.

The present invention is concerned with a process for the expression of a recombinant gene which contains AGA and/or AGG codons for arginine in *Escherichia coli* after transformation with an expression vector which contains the recombinant gene.

The gene-technological production of proteins or protein-containing gene products is one of the main objects of modern biotechnology. Since, in particular, prokaryotes are suitable for the production of comparatively large amounts of protein because of their easy fermentability, attempts have already been made many times to express eukaryotic genes in prokaryotes. However, difficulties arise since eukaryotic proteins are often only produced in small amounts in prokaryote cells and the cells show fermentation/growth difficulties in the case of increased production of the proteins.

Such problems are observed, inter alia, in the case expression of the tissue type plasminogen activator t-PA. However, the production of this protein is an object worth striving for since, in clinical trials, it has proved to be suitable for the treatment of infarct diseases. Although *E. coli* cells express t-PA cDNA introduced on a plasmid or vector in a satisfactory amount, nevertheless the cells weaken in the case of the formation of biomass during the fermentation so that, in all, the production of t-PA does not reach the state which could be expected when starting from the production of a single cell. The plasmid stability in the *E. coli* cells is also low and, due to loss of the coding plasmid, the rate of production decreases further. Therefore, hitherto it has only been possible to achieve an expression of about 5% of the total cell protein as t-PA (Rothstein and Bertonis, Gene, 61, 41–50/1987).

It is an object of the invention to provide a process for enhanced yield of expression of gene products. The process is superior to known processes where notably poorer growth of host cells, as well as plasmid instability was observed. Both factors led to low yields of gene product.

Thus, according to the present invention, there is provided a process for the expression of a recombinant gene, which contains AGA and/or AGG codons for arginine, in *Escherichia coli* after transformation with an expression vector which contains the recombinant gene, wherein the amount of t-RNA present in the *E. coli* cells which incorporates arginine and recognizes the codons AGG and AGA is increased to at least fivefold of the amount normally occurring in these cells.

In the scope of the present invention, by the term t-RNA which recognizes AGA/AGG codons and incorporates arginine, there is to be understood not only the corresponding t-RNA occurring naturally in *E. coli* but also those synthetic, mutated or suppressor t-RNA's which display these properties.

The process according to the present invention makes it possible to produce, in distinctly increased amounts, recombinant genes whose expression in the past led to only low yields of the desired proteins because of poor growth of the *E. coli* host cells. This result is unexpected because, when there is a shortage of t-RNA, protein synthesis would be expected to be low due to poor expression of the foreign gene. In fact, the foreign gene is well expressed, but the host cell suffers.

In a preferred embodiment of the present invention, the amount of t-RNA which recognises the AGA/AGG codon and incorporates arginine, hereinafter simply referred to as t-RNA, is increased in the *E. coli* cells by introducing into the cells at least one gene coding for such t-RNA. This can preferably take place by introducing one or more extra-chromosomal expression vector into the cell.

The natural t-RNA which incorporates arginine into *E. coli* and recognizes the codons AGA and AGG is a product of the dnaY gene which was described by Garcia et al. in Cell, 45, 453–459/1986. The whole sequence of this gene is known: it contains 118 essential base pairs and is preferably used for increasing the amount of t-RNA in *E. coli* by introduction of the gene. However, it is also possible to introduce into the cells a gene for a synthetic, mutated or suppressor t-RNA which incorporates arginine and recognizes the AGA/AGG codon. It is also possible to use the gene of the t-RNA of the phage $T_4$.

In a preferred embodiment of the present invention, the t-RNA gene or genes, together with the eukaryotic gene, are introduced on the same expression vector into the cell. When the expression vector is a high copy plasmid, there is thereby already provided a sufficient increase of the intracellular t-RNA level so that no negative effects are to be observed on the host cells in the case of the expression of the eukaryotic gene.

In another preferred embodiment, the t-RNA gene and the eukaryotic gene are introduced on different expression vectors into the *E. coli* cells. The positive effect of making available a t-RNA Arg(AGG/AGA) during the expression of recombinant protein in *E. coli* is, not dependent upon the fact that the gene for this t-RNA is present in the cis-position on the expression vector in question. This t-RNA can also be coded on a second vector (trans-active). However, this additional vector must be compatible with the expression vector in the *E. coli* cell, i.e. have a replication origin different from that of the expression plasmid.

It is possible to use a vector with a smaller plasmid copy number than the expression plasmid but also, by the use of a vector which is present in higher copy number than the expression vector on which the eukaryotic gene is present, to achieve a still higher t-RNA level in comparison with the eukaryotic gene. In the case of the introduction of the t-RNA gene and of the eukaryotic gene on the same expression vector, it is not only possible to use two genes under the control of different promoters but also both genes in the form of an operon under the control of the same promotor. The only thing that is important is that a stop codon is present between the eukaryotic gene and the t-RNA gene so that no fusion protein is obtained following transcription.

In another preferred embodiment of the present invention, the t-RNA gene or genes is or are incorporated into the chromosome of the host cell. It is especially preferred to integrate the gene in such a manner that it is expressed under a strong promoter. For this purpose, the t-RNA gene or genes is or are preferably introduced simultaneously, together with a strong promotor under the control of which the t-RNA is expressed.

Known methods are used for the introduction of a t-RNA gene into the chromosome, as well as for the introduction of the gene into an expression vector, as well as for the transformation of the host cells. For the introduction into the chromosome, methods which use transposons or phages, and use recombination phenomena are preferred A further preferred possibility of increasing the amount of t-RNA in the cell is to change the natural promotor of the chromosomal gene which codes for this t-RNA in such a way that the t-RNA is formed in larger amounts. For this purpose, it is especially preferred to exchange the whole natural promotor for a stronger, preferably inducable and/or repressable promotor. Such promotors are known to the expert, as well as the processes for the exchange of the promotors which again are preferably carried out with the use of transposons or phages.

The present invention also provides a process for the expression of a recombinant gene which contains AGA and/or AGG codons for arginine in *E. coli* by transformation with an expression vector which contains the recombinant gene, wherein an *E. coli* strain is selected which contains at least the fivefold amount of the amount of t-RNA normally occurring in *E. coli* which recognizes the codons AGG and AGA and incorporates arginine, this strain being used as host cell.

Previously known strains mostly have only a small amount of t-RNA which incorporates arginine and which recognises the codons AGA/AGG and there occur the results described hereinbefore in the case of the expression of a foreign gene. As standard for *E. coli* strains with the normal small amount of the t-RNA used according to the present invention, there can be mentioned, for example, the strains DSM 3689, DSM 2102, HFR 3000 and C600 (DSM 2093) (the latter two are described by Bachmann, Bacteriol. Rev., 36, 180–230/1972). According to the process of the present invention, *E. coli* strains can now be found which themselves contain a higher, namely at least the doubled amount of this t-RNA. For this purpose, selection is preferably carried out in such a manner that whole RNA of the *E. coli* cells is obtained and this is hybridized against a labelled oligonucleotide which corresponds to a specific part of the DNA sequence of the t-RNA. The, the Northern blot technique is preferably used. The Northern blot technique is known to the expert and has been described, for example, by Maniatis et al., Molecular Cloning, A Laboratory Manual, Cold Spring Harbor Laboratory, Cold Spring Harbor, N.Y., 1982. For the hybridization, a radio-active labelled oligonucleotide is preferred but all other labels can advantageously be used for the DNA fragments. The phase a specific part of the DNA sequence of the t-RNA which recognizes the codons AGG and/or AGA, is to be understood to mean the DNA sequences on or in the direct neighborhood of the anticodon in the t-RNA, the so-called anticodon loop. In contradistinction to the pseudouridine or dihydrouridine loop, this region of a t-RNA is not very homologous to other t-RNA's so that an oligonucleotide of the sequence 5'-CACGACTTAGAAGGTCGTTG-3' or also, for example, of the shorter sequence 5'-GACTTAGAAGGTCGTT-3', as well as in each case the complementary oligonucleotides (5'-CAACGACCTTCTAAGTCGTG-3'; 5'-AACGACCTTCTAAGTC-3') can be used as specific probe for the detection and characterization of this t-RNA. According to the present invention, an oligonucleotide is preferably used which has a length of from 14 to 30 base pairs.

The process according to the present invention can be used for all recombinant genes, eukaryotic genes or the cDNA thereof preferably being expressed and especially those which contain a comparatively large number of AGG and/or AGA codons. These include, for example, human urokinase, t-PA or derivatives thereof, HIV proteins (for example gp41 and p24) and α-glucosidase from yeast. A great advantage of the process according to the present invention is the fact that the recombinant genes can be expressed constitutively.

The process according to the present invention is especially preferred for the production of t-PA in that, as recombinant gene, there is expressed the t-PA gene (described by Pennica et al., Nature, 301, 214–221/1983) or a variant thereof. In comparison with the expression rates previously known from the prior art of about 5% t-PA per *E. coli* total cell protein, according to the present invention, the yield can be increased to more than 30%. This means a 600% increase of the yield with the help of the process according to the present invention.

In a further preferred embodiment of the present invention, the plasmid pUBS 98.sky1, DSM 4898, is expressed in *E. coli* which contains the gene for t-PA and the dnaY gene.

The present invention also provides expression vectors which contain a recombinant gene and a gene for t-RNA which incorporates arginine or recognizes the codons AGG and/or AGA. Both genes can each stand under the control of different promotors, in which case there can be used the promotors homologous for the gene in question but also heterologous promoters and also, according to a preferred embodiment of the present invention, stand under the control of a common promotor in the form of an operon.

An expression vector which is preferably used for the cloning and expression of recombinant genes in *E. coli* comprises a constitutive or regulatable promotor transcribable in *E. coli* (e.g. lac, tac, trp, *E. coli* ribosomal promoters, *Bacillus stearothermophilus* α-galactosidase promotor), optionally followed by a ribosome binding position for the translation initiation, optionally followed by a translation initiation codon (preferably ATG), followed by a polylinker for the cloning of the gene/cDNA to be expressed, optionally followed by an m-RNA-stabilizing sequence, followed by a transcription terminator (preferably fd terminator), a resistance gene (preferably kanamycin-resistance gene), a replication origin capable of stable plasmid propagation in *E. coli* as well as a gene for a t-RNA Arg (AGG/AGA).

A plasmid especially preferred according to the present invention is pUBS 98.sky1, DSM 4898. The plasmid contains not only the dnaY gene but also the t-PA gene.

The present invention also provides expression auxiliary vectors which contain a gene for t-RNA which incorporates arginine and recognizes the codons AGG and/or AGA and possess a replication origin different from the ColE1 plasmids and their derivatives.

It is thus possible to co-culture together the thus mentioned expression auxiliary vector and a ColE1 expression vector in *E. coli* cells.

In a preferred embodiment of the present invention, gene for the t-RNA stands under the control of its natural *E. coli* promotor i.e., a homologous promotor. In another preferred embodiment the t-RNA gene is under the control of a heterologous promotor. In an especially preferred embodiment, the promotor is of the lac, tac, mgl or trp promotor or the α-galactosidase promotor from *Bacillus stearothermophilus*.

The present invention is also concerned with the use of the above expression vectors for the expression of the recombinant gene present therein, greatly increased yields thereby being obtained, and with the use of the above-mentioned expression auxiliary vectors for increasing the yield of the expression of the gene which is introduced into an *E. coli* cell in the form of a recombinant DNA suitable for the expression of the gene. According to the present invention, in the case of the use of a constitutive promotor, the recombinant gene can thereby be constitutively expressed.

DETAILED DESCRIPTION OF PREFERRED EMBODIMENTS

EXAMPLE 1

Figure 1:
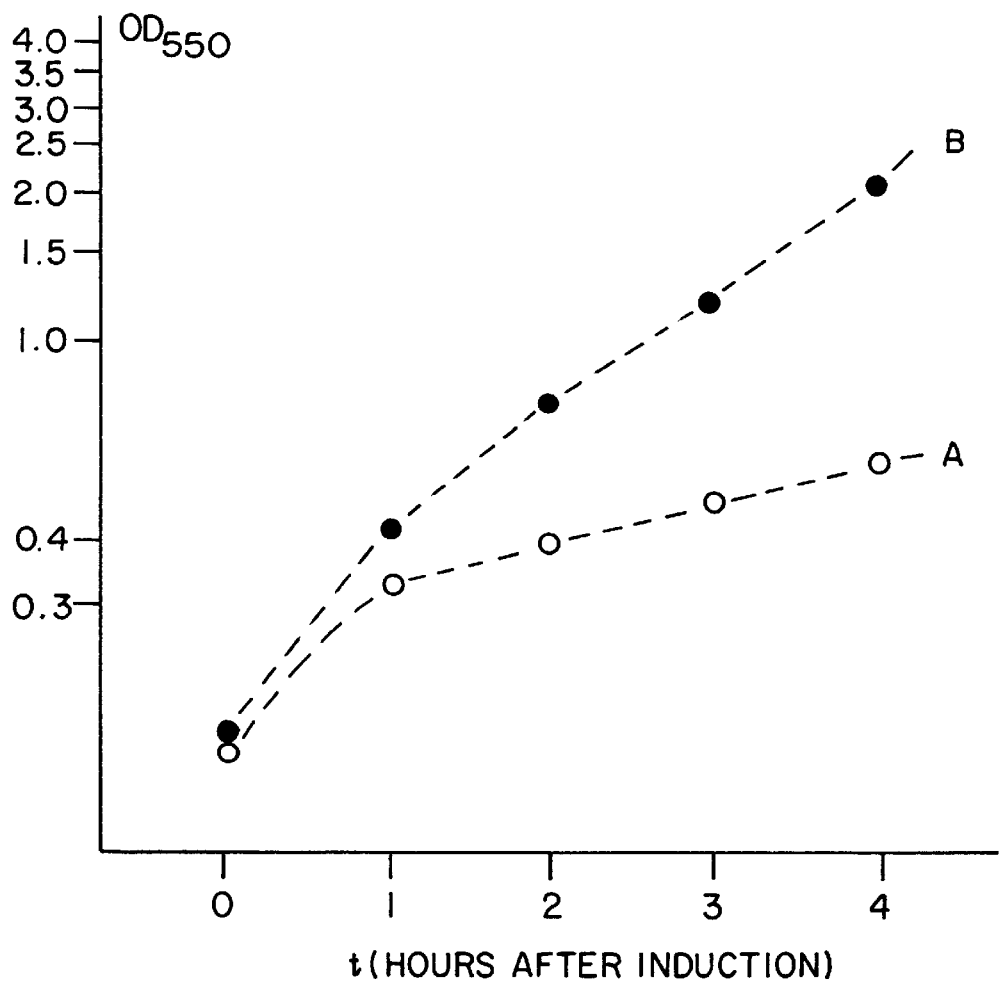
FIG. 1 shows increased expression of a gene for t-PA, when induced and co-transfected with an expression plasmid in accordance with the invention.

Construction of t-PA Expression Plasmids.

a) Plasmid pePa 126.1

The plasmid pePa 98.1 (see European Patent Specification No. 0,242,836) was used as starting plasmid for the construction of an improved t-PA expression plasmid. The about 400 bp long 3'-untranslated region of the t-PA cDNA in this plasmid was shortened, by the deletion of a 361 bp long Xho II fragment, to about 40 bp. The resultant plasmid has been given the name pePa 126.1 and can be differentiated from pePa 98.1 because when these plasmids are subjected to double digestion with Bam HI and HindIII, pePA 98.1 yields two fragments having lengths of 2234 and 4372 base pairs, whereas pePA 126.1 yields two fragments having 1873 and 4372 base pairs b) Plasmid pUBS 98. sky1.

The expression plasmid pUBS 98. sky1 contains an approximately 3000 bp sized Dra I fragment of plasmid pDM 201 which contains a gene (dnaY) for a t-RNA Arg (AGG/AGA) (Garcia et al., Cell, 45, 453–459/1986) which was inserted in a Dra I-cleaved t-PA expression plasmid which is a kanamycin-resistant derivative of the above-described plasmid pePa 126.1. pUBS.sky1 was deposited on Oct. 28, 1988 under the number 4898 at the German Collection for Micro-organisms (Deutsche Sammlung von Mikoorganismen (DSM)), Gesellschaft fur Biotechnologische Forschung mbH, Griabachstrasse 8D-3400, Gottingen, Germany.

EXAMPLE 2

Expression of t-PA in *E. coli* with an Expression Auxiliary Plasmid.

The gene for the t-RNA Arg(AGG/AGA) was cloned on a plasmid which is compatible with the t-PA expression vector pePa 126.1 which possesses a Cole1 replication origin (is a pBR322 derivative).

Plasmid pACYC 177 (Chang and Cohen, J. Bact., 134, 1141–1156/1978), DSM 3693P, was, for this purpose, cleaved with Dra I and a 3230 bp fragment isolated. This fragment was ligated with the approximately 3000 bp Dra I fragment from plasmid pDM 201, which contains the dnaY gene, and the ligation batch transformed in *E. coli*, DSM 2102.

The kanamycin-resistant clones which contain the plasmid pUBS 400 or pUBS 401, were identified by colony filter hybridization with the oligonucleotide [5'-AGCAACGACCTTCTAAGTCGTGGG-3'] and isolated. The plasmids pUBS 400 and pUBS 401 isolated in this way differ from pACYC 177 by a 3000 bp insert in the Dra I cleavage position on which is present the gene for a t-RNA Arg(AGG/AGA) and, between themselves, in the orientation of the 3000 bp Dra I insert (Example 1) in the vector.

The plasmid pUBS 400 is characterized by an approximately 3300 base pair fragment following HindII/HindIII double digestion, via Southern analyses. This fragment hybridizes with synthetic oligonucleotide [5'-AGCAACGACCTTCTAAGTGGTGGG-3']. The plasmid pUBS401 yields a fragment of approximately 1700 base pairs, under the same conditions, which also hybridizes the aforementioned synthetic oligonucleotide.

The plasmid pIQ 500 is a pACYC 177 derivative which contains the lac I$^q$ gene. The plasmid pIQ 500 contains the lac I gene (P. J. Farabaugh, Nature, 274, 765–769/1978) with the iq promotor mutation (Calos, Nature, 274, 762–765/1978) as Hind II fragment (partly from pMCl, Calos, 1978 v. supra) inserted in Hind II-cleaved plasmid pACYC 177 Chang and Cohen, J. Bact., 134, 1141–1156/1978).

pIQ 500-containing *E. coli* cells are kanamycin-resistant and in contradistinction to pACYC 177-containing *E. coli* cells, are ampicillin-sensitive and contain a substantially higher concentration of Lac repressor molecules (lac I) than comparable *E. coli* without this plasmid. pIQ 500 was used for the support of the repression of recombinant genes in the non-induced state insofar as these genes are transcribed under the control of the lac promotor or derivatives, for example tac, trc or the like, and the expression plasmids are compatible with pIQ 500, for example pKK 223-3 derivatives.

The cloning of a t-RNA-Arg (AGG/AGA) gene onto this plasmid, in addition to the lac I$^q$ gene makes it possible for the *E. coli* cells to provide not only the amounts of lac repressor necessary for the repression in the non-induced state but also the large amounts of t-RNA-Arg (AGG/AGA) needed during the expression of eukaryotic proteins.

Plasmid pIQ 500 was cleaved with Dra I and a 4836 bp fragment was isolated. This fragment was ligated with the approximately 3000 bp Dra I fragment from plasmid pDM 201, which contains the dnaY gene, and the ligation batch transformed in *E. coli*, DSM 2102.

Kanamycin-resistant clones which contain the plasmid pUBS 500 or pUBS 501 were identified and isolated with the synthetically produced oligonucleotide [5'-AGCAACGACCTTCTAAGTCGTGGG-3'].

The plasmids pUBS 500 and pUBS 501 isolated in this manner differ from pIQ 500 by a 3000 bp insert in the Dra I cleavage position on which is present the gene for a t-RNA Arg (AGG/AGA) and, between one another, in the orientation of the 3000 bp insert in the vector. pUBS is thereby characterized in that in Southern blot analyses of Hind II-digested plasmid DNA, an approximately 4000 bp fragment hybridizes with the synthetic oligonucleotide [5'-AGCAACGACCTTCTAAGTCGTGGG-3']. pUBS is characterized in that, in analyses carried out analogously, an approximately 1700 bp fragment hybridizes to the above synthetic oligonucleotide.

The expression auxiliary plasmids pUBS 400 and pUBS 500 are able transactively to compensate the negative effects of the t-PA expression with the plasmid pePa 126.1 by making available the needed t-RNA Arg (AGG/AGA).

Expression in the case of co-transformation of available *E. coli* laboratory strains, for example C-600, with plasmid pUBS 400 or pUBS 500 and pePa 126.1 lead to yields and vitality as in the case of t-PA production with pUBS 98.sky1.

The following Table 1 and FIG. 1 of the accompanying drawing show the comparison of the expression of recombinant t-PA from pePa 126.1 in *E. coli*, DSM 2102, co-transformed with pIQ 500 (sample A) or pUBS 500 (sample B) in the case of induction with 5 mM IPTG.

TABLE 1

| sample | E. coli plasmid | % rec. protein (intact t-PA) total protein | OD 550 in the case of induction | OD 550 3 hrs. after induction |
|---|---|---|---|---|
| A | E. coli DSM 2102 + pePa 126.1 + piq 500 | 2–5 | 0.1 | 0.4 |

TABLE 1-continued

| sample | E. coli plasmid | % rec. protein (intact t-PA) total protein | OD 550 in the case of induction | OD 550 3 hrs. after induction |
|---|---|---|---|---|
| B | E. coli DSM 2102 + pePa 126.1 + pUBS 500 | >30 | 0.1 | 1.2 |

EXAMPLE 3
Comparison of the Expression of t-PA in E. coli.

The plasmids pePa 133 (Federal Republic of Germany Patent Specification No. 36 13 401), pePa 126.1 (Example 1) and pUBS 98.sky1, DSM 4898 were transformed in E. coli, DSM 3689 which contains an I$^q$ plasmid. Transformants were cultured on LB plates (Maniatis, 1982, v. supra) with 25 μg./ml. kanamycin (in the case of pePa 133 and pUBS.sky1) and 50 μg./ml. ampicillin in the case of pePa 126.1).

Plasmid-containing cells were cultured in LB up to OD 550 nm=0.3, induced by the addition of 10 mmol/l. IPTG and fermentated at 37° C. The growth of the cultures was monitored by measurement of the cell density (OD 550) at regular intervals.

4 hours after induction, the cells were harvested and digested by ultrasonic treatment. The so obtained cell lysate was analyzed electrophoretically (Coomassie blue-coloured SDS gels) and t-PA was detected in Western blots with polyclonal antibodies against t-PA from goats and quantified via densitometric evaluation of Coomassie-coloured SDS gels after previous protein determination of the cell lysate.

The following Table 2 shows a comparison of the yields and of other parameters in the case of the expression of the said plasmids in E. coli, DSM 3689.

The t-PA expression with plasmid pePa 133 has already been described in Federal Republic of Germany Patent Specification No. 36 13 401.

The expression with plasmid pePa 126.1 impairs the growth of E. coli in 5 ml. roll cultures only insubstantially but substantially on the fermentation scale (>10 liters) and, furthermore, produces intact t-PA only in a small amount instead of this t-PA fragments in large amounts.

Expression of t-PA in E. coli with plasmid pUBS.sky1 makes possible a very high expression capacity of intact t-PA's (30% of the total cell protein) without negative effects on the production organism. t-PA-producing cells grow very quickly with this plasmid and to high cell densities and t-PA can even be expressed constitutively.

EXAMPLE 4
Comparison of the Expression of Various Proteins in E. coli With and Without Expression Auxiliary Plasmid.

The plasmids pUPA 110 (containing the sequence for human pro-urokinase without signal peptide, Holmes et al., Biotechnology, 3, 923–929/1985), pGP41 (containing the coding sequence for the p41 protein of the human HIV virus, Ratner et al., Nature, 313, 277–284/1985), pKK 177-3/GLUCPI (containing the sequence for α-glucosidase from yeast, European Patent Specification No. 0 300 425), pBT 102 (DSM 2091) (α-glucosidase from E. coli) and plasmid pUR 289 (containing the sequence for β-galactosidase from E. coli, Rüther and Mulker, EMBO J., 2, 1791–1794/1983) were transformed in E. coli, DSM 3689, which contains an I$^q$ plasmid. The culturing of the transformants, as well as the fermentation, were carried out analogously to Example 3.

The following Table 3 shows the comparison of the expression of the recombinant proteins with and without the expression auxiliary plasmid pUBS 500.

TABLE 3

| 1. plasmid | 2. plasmid | % recombinant protein, referred to total amount of protein | OD 550 in the case of induction | OD 550 in the case of harvesting | vitality of the cells in the case of expression |
|---|---|---|---|---|---|
| pUPA 110 | piq 500[2] | 7% | 0.15 | 0.70 | (−) |
| pUPA 110 | pUBS 500 | >30% | 0.15 | 1.30 | + |
| pGP 41 | piq 500 | <2% | 0.10 | 0.20 | − |
| pGP 41 | pUBS 500 | >30% | 0.10 | 0.90 | + |
| pKK 177-3 | piq 500 | 15% | 0.15 | n.d.[1] | (+) |
| pKK 177-3 | pUBS 500 | 30% | 0.15 | n.d. | + |
| pUR 289 | piq 500 | 20% | 0.15 | n.d. | (+) |
| pUR 289 | pUBS 500 | 30% | 0.15 | n.d. | + | n.d.[1] not measured
[2] piq 500 is the base plasmid of pUBS 500 without t-RNA-Arg (AGG/AGA) gene

TABLE 2

| plasmid | t-PA qualit. | yield intact | vitality | plasmid stability |
|---|---|---|---|---|
| pePa 133.6 | intact | 3–5% | good | n.d. |
| pePa 126.1 | fragments | 5% | poor | poor |
| pUBS 98.skyl. | intact | >30% | good | good | n.d. = not measured.

What is claimed is:
1. A method for increasing production of a protein which contains arginine, comprising the steps of:
(i) transforming an Escherichia coli host cell with an expression vector which contains a DNA sequence, wherein said DNA sequence (a) codes for the arginine containing protein, and (b) contains codons AGG and AGA;
(ii) transforming said Escherichia coli host cell with an extrachromosomal expression vector which contains a DNA sequence which codes for a tRNA, wherein said tRNA (a) incorporates arginine into protein, (b) recog- nizes both of codons AGA and AGG, and (c) contains anticodon UCU, and (iii) treating the transformed host cell resulting from step (ii) under conditions favoring an increase in expression of said DNA sequence which codes for said tRNA, so as to produce the arginine containing protein in an amount greater than the amount of the arginine containing protein that could be produced by the transformed host cell prior to step (ii).

2. The method of claim 1, wherein said DNA sequence which codes for said tRNA and said DNA sequence which codes for the arginine containing protein are positioned on the same extrachromosomal expression vector.

3. The method of claim 1, wherein said DNA sequence which codes for said tRNA and said DNA sequence which codes for the arginine containing protein are positioned on two different extrachromosomal expression vectors.

4. The method of claim 1, wherein said DNA sequence which codes for the tRNA is a dnaY gene.

5. The method of claim 1, wherein said DNA sequence which codes for the arginine containing protein is a eukaryotic gene or cDNA.

6. The method of claim 1, wherein the DNA sequence which codes for the arginine containing protein is a eukaryotic gene or cDNA sequence which codes for human tissue type plasminogen activator.

7. The method of claim 2, wherein said same extrachromosomal expression vector is plasmid pUBS 98.sky1 (DSM 4898).

8. Plasmid pUBS 98.sky1 (DSM 4898).

9. A method for enhanced expression of a gene which codes for an arginine containing protein, comprising: transforming an *Escherichia coli* host cell with: a first vector which contains (i) a gene which codes for tRNA which (a) incorporates arginine into a protein, (b) recognizes both codon AGA and codon AGG and (c) contains the anticodon UCU, and (ii) a first ori; and a second vector which contains (i) a DNA sequence which (a) codes for the arginine containing protein and (b) contains AGA and AGG codons, and (ii) a second ori different from said first ori, and culturing the transformed *Escherichia coli* host cell under conditions favoring an increase in the expression of said gene which codes for said tRNA, so as to produce the arginine containing protein in an amount greater than the amount of the arginine containing protein that could be produced by an *E. coli* host cell which is not transformed with said first vector, wherein said tRNA incorporates arginine into the arginine containing protein.

10. The method of claim 9, wherein said second ori is a ColE1 ori.

* * * * *